United States Patent [19]
Purdy et al.

[11] 3,987,799
[45] Oct. 26, 1976

[54] HEART PACER
[75] Inventors: David L. Purdy, Indiana; George J. Magovern, Pittsburgh, both of Pa.; Nicholas P. D. Smyth, Washington, D.C.
[73] Assignee: Coratomic Inc., Indiana, Pa.
[22] Filed: Feb. 14, 1975
[21] Appl. No.: 550,071

Related U.S. Application Data
[63] Continuation-in-part of Ser. No. 378,636, July 12, 1973, Pat. No. 3,866,616.

[52] U.S. Cl. ........................................... 128/419 P
[51] Int. Cl.² ........................................ A61N 1/36
[58] Field of Search ...... 128/419 E, 419 P, 419 PG, 128/419 PS

[56] References Cited
UNITED STATES PATENTS
3,421,512  1/1969  Frasier ........................... 128/419 PS
3,867,950  2/1975  Fischell .......................... 128/419 PG OTHER PUBLICATIONS
USCI Catalog No. 5070072, Aug. 1972, 4 pages.

Primary Examiner—William E. Kamm
Attorney, Agent, or Firm—Hymen Diamond

[57] ABSTRACT
A heart pacer to be implanted between the pectoralis major muscle and the skin a short distance below the clavicle having an outer container in the shape of an ovaloid. Such a heart pacer adapts itself positionally, cosmetically and with a minimum of discomfort to implantation.

5 Claims, 7 Drawing Figures

U.S. Patent     Oct. 26, 1976     3,987,799
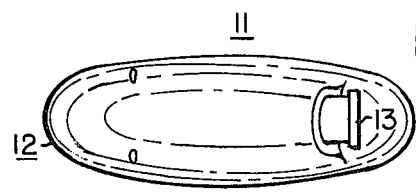
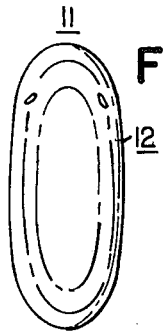
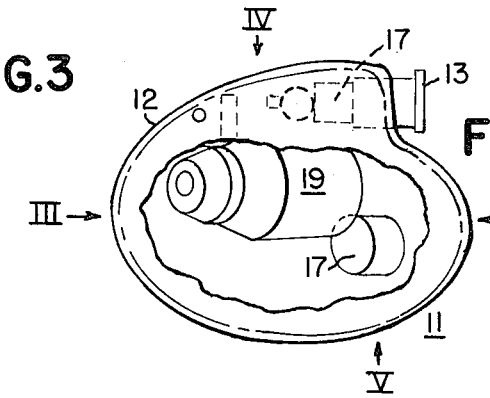
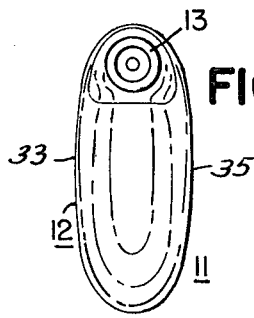
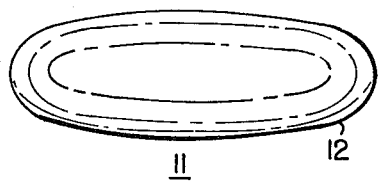
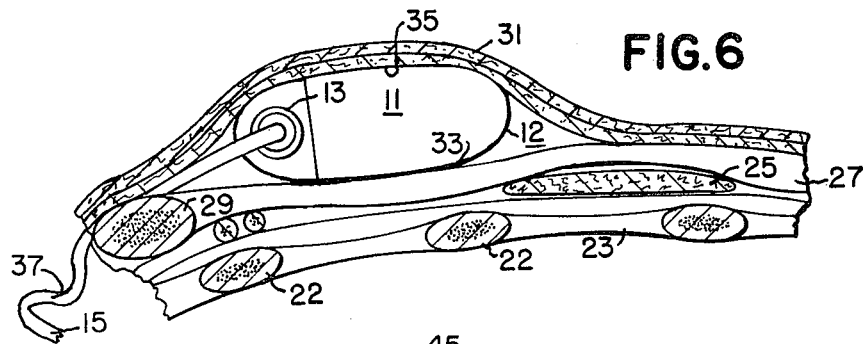
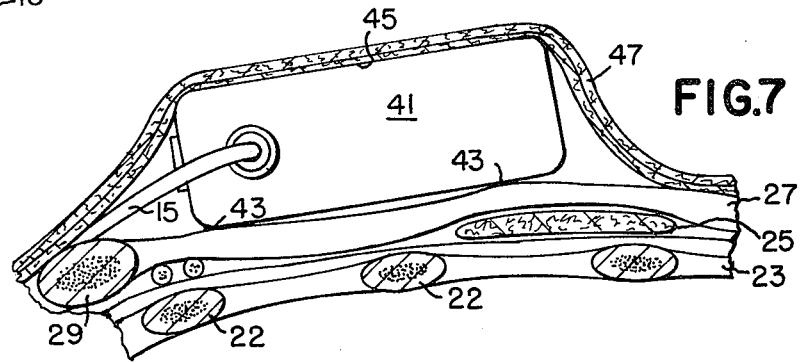

HEART PACER

REFERENCE TO RELATED APPLICATIONS

This application is a continuation-in-part of application Ser. No. 378,636 filed July 12, 1973, now U.S. Pat. No. 3,866,616 granted Feb. 18, 1975 to David L. Purdy, George J. Magovern and Nicholas P. D. Smyth for Heart Pacer and assigned to CORATOMIC INC.

BACKGROUND OF THE INVENTION

This invention relates to heart pacers and has particular relationship to heart pacers which are implanted in human beings. It has become the practice to implant such heart pacers in the chest, usually on the left, a short distance below the clavicle or collar bone. The pacer so installed rests between the pectoralis major muscle and the skin engaging the skin outwardly of this muscle. Typically the conductor from the pacer which supplies the pulsations is passed upwardly over the clavicle and is connected to the heart through a vein adjacent the clavicle.

In accordance with the teachings of the prior art the outer container of the pacer has the form of a rectangular parallelapiped with rounded corners. Such a pacer does not fit into the biological contour of the body where it is installed and is subject to expulsion. In addition, the edges of the pacer container produce an unsightly protrusion of the skin and the engagement of these edges and the corners with the skin causes discomfort and tends to cause skin necrosis.

It is an object of this invention to overcome the above-described difficulties and disadvantages of the prior art and to provide a heart pacer to be implanted in the chest of a human being that shall fit into the biological contour of the body where it is implanted and shall be readily acceptable by the body, shall be cosmetic, shall not have a tendency to cause skin necrosis and shall be readily implantable in a wide variety of sites in the body.

SUMMARY OF THE INVENTION

In accordance with this invention a heart pacer is provided which has an outer container of generally ovaloid form. This pacer seats neatly in the pectoralis major muscle minimizng any tendency for the muscle to expel the pacer. The skin adapts itself readily to this pacer minimizing unsightly protrusions. The pacer has no edges or ends which engage the skin and tend to cause skin necrosis.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 1 is a view in side elevation, with a part of the wall broken away, of a heart pacer in accordance with this invention;

FIG. 2 is a view in end elevation as seen from the direction of the arrow II of the pacer shown in FIG. 1;

FIG. 3 is a view in end elevation from the direction of the arrow III of the pacer shown in FIG. 1;

FIG. 4 is a plan view from the direction of the arrow IV of the pacer shown in FIG. 1;

FIG. 5 is a plan view from the direction of the arrow V of the pacer shown in FIG. 1;

FIG. 6 is a fragmental view in section of a part of a human body showing the manner in which the heart pacer according to this invention is implanted; and FIG. 7 is a like fragmental view in section of the human body showing the manner in which a pacer in accordance with the prior art is implanted.

DETAILED DESCRIPTION OF THE INVENTION

The apparatus shown in FIGS. 1 through 5 is a heart pacer 11 including a generally ovaloid container 12 whose contours viewed in different directions or sections (FIGS. 2 and 3 parent patent 2,866,616) are of elliptical form. The container has a head 13 encased in transparent resin (epoxy) from which a catheter 15 (FIG. 6) extends. The catheter 15 is connected to a terminal block 17. Within the container there is a power supply 19 and an electrical circuit 21 for deriving pulsations from the supply 19. The pulsations are supplied to the heart through the catheter. The power-supply 19 and the other components are shown in detail in the parent U.S. Pat. No. 2,866,616.

Typically, the heart pacer 11 has an overall length of 2.45 inches, a width of 1.88 inches and a depth of 0.80 inch.

In FIGS. 6 and 7 there are shown some of the members of the human body in which a pacer is implanted. The section is taken along the body between the head above and the feet below. The members include the ribs 22 between which the intercostal muscle 23 extends. Outwardly of the ribs 22 are the pectoralis minor muscle 25 and the pectoralis major muscle 27. The pectoralis major muscle 27 extends from the clavicle or collar bone 29. The skin 31 extends outwardly of the pectoralis major muscle 27 and the clavicle 29.

The pacer 11 according to this invention is implanted with its side 33 engaging, and neatly seated on, the pectoralis major muscle 27 and the opposite side 35 engaging the skin 31. The pacer fits neatly against the skin 31 and does not produce an unsightly bulge. The catheter 15 is passed over the clavicle 29, is provided with a loop 37 above the clavicle 29 and then is passed through a vein (not shown) to the heart.

On the contrary the prior-art pacer 41 (FIG. 7) does not seat on the pectoralis major muscle 27 but engages it at isolated points 43. The skin 31 engages this pacer 41 along its edges 45 and, because the deformation of the skin 31 is sharp as shown at 47 rather than gradual as for the pacer according to this invention, an unsightly protrusio is produced.

While a preferred embodiment of this invention has been disclosed herein, many modificatons thereof are feasible. This invention is not to be restricted except insofar as is necessitated by the spirit of the prior art.

We claim:

1. A heart pacer including a container having therein power-supply means and means for deriving pulsations to be supplied to the heart from said power-supply means, said container to be implanted a short distance below the clavicle of the human body, said container having the form generally of an ovaloid its contour as viewed from its ends, its top and bottom and its sides, being of generally oval 0 configuration whereby said pacer adapts itself positionally and cosmetically and with a minimum of discomfort to the region of the human body where it is implanted.

2. The heart pacer of claim 1 wherein the contour of the container as viewed in the directions of its ends, of its top and bottom and of its sides is of generally elliptical configuration.

3. The heart pacer of claim 1 to be implanted between the pectoralis major muscle and the epidermis of the host, the dimensions in connection with the ovaloid contour of the container of the pacer being such that said container seats neatly in the pectoralis major muscle and in the epidermis without producing an unsightly bulge of the epidermis.

4. The heart pacer of claim 1 having a container which has substantially no sharp corners in the region where it is seated in the body.

5. The heart pacer of claim 1 having a terminal for connecting a catheter, said terminal extending generally tangentially from a surface of the container.

* * * * *